US008133678B2

(12) United States Patent
Ellis et al.

(10) Patent No.: US 8,133,678 B2
(45) **Date of Patent: *Mar. 13, 2012**

(54) COT102 INSECTICIDAL COTTON

(75) Inventors: Daniel Murray Ellis, Research Triangle Park, NC (US); David Vincent Negrotto, Research Triangle Park, NC (US); Liang Shi, Research Triangle Park, NC (US); Frank Arthur Shotkoski, Research Triangle Park, NC (US); Carla Randall Thomas, Taylors, SC (US)

(73) Assignee: Syngenta Participations AG, Basel (CH)

( * ) Notice: Subject to any disclaimer, the term of this patent is extended or adjusted under 35 U.S.C. 154(b) by 20 days.

This patent is subject to a terminal disclaimer.

(21) Appl. No.: 12/849,550

(22) Filed: Aug. 3, 2010

(65) Prior Publication Data

US 2010/0298553 A1 Nov. 25, 2010

Related U.S. Application Data

(62) Division of application No. 11/853,243, filed on Sep. 11, 2007, now Pat. No. 7,803,547, which is a division of application No. 10/530,234, filed as application No. PCT/EP03/011725 on Oct. 23, 2003, now Pat. No. 7,371,940.

(30) Foreign Application Priority Data

Oct. 29, 2002 (GB) .................................. 0225129.6

(51) Int. Cl.
*C12Q 1/68* (2006.01)
*C12P 19/34* (2006.01)

(52) U.S. Cl. ..................... 435/6.12; 435/91.2; 536/22.1; 536/24.3

(58) Field of Classification Search ............. 435/6, 91.2, 435/6.12; 536/22.1, 24.3
See application file for complete search history.

(56) References Cited

U.S. PATENT DOCUMENTS 7,371,940 B2 * 5/2008 Ellis et al. .................... 536/23.1
7,803,547 B2 * 9/2010 Ellis et al. ......................... 435/6
2003/0073623 A1 4/2003 Demanac et al.
2003/0204075 A9 10/2003 Wang et al.

FOREIGN PATENT DOCUMENTS

| | | | |
|---|---|---|---|
| EP | 142924 | A2 | 5/1985 |
| WO | WO9610083 | | 4/1996 |
| WO | WO9844137 | | 10/1998 |
| WO | WO02078437 | A2 | 10/2002 |
| WO | WO03075655 | A2 | 9/2003 |

OTHER PUBLICATIONS

Barth, et al., The update machinery of clostridial actin ADP-ribosylating toxins—a cell delivery system for fusion proteins . . . , Naunyn-Schmiedeberg (2002) 366:501-512.

Liao, et al., Toxicity of *Bacillus thuringiensis* insecticidal proteins for *Helicoverpa armigera* and *Helicoverpa punctigera* . . . Journal of Invertebrate Pathology 80 (2002) 55-63.

Birren, et al., *Mus musculus* clone RP24-21711, Working draft sequence, 4 unordered pieces. Database accession No. AC120146.

Rothstein, et al., Promoter cassettes, anti-biotic-resistance genes, and vectors for plant transformation. Gene (1987) 53: 153-161.

Umbeck., et al., Genetically transformed cotton (*Gossypium hirsutum* L.) plants. Biotechnology (1987) 5:263-266.

Rajguru., et al., Assessment of resistance of cotton transformed with lectin genes . . . (*Heliothis virescens*), Proceedings of the Beltwide Cotton Conference (1998) 1:490-491.

Fujiyama, et al., 2002, GenBank Accession No. AG142557.

Alonso, et al., 2002, GenBank Accession No. BH863748.

* cited by examiner

*Primary Examiner* — Kenneth R. Horlick
*Assistant Examiner* — Joyce Tung
(74) *Attorney, Agent, or Firm* — Christoper L. Leming

(57) ABSTRACT

The present application relates to an insect resistant transgenic cotton plant. In particular, it relates to a specific event, designated COT102. The application also relates to polynucleotides which are characteristic of the COT102 event, plants comprising said polynucleotides, and methods of detecting the COT102 event. The COT 102 event exhibits a novel genotype comprising two expression cassettes. The first cassette comprises a suitable promoter for expression in plants operably linked to a gene that encodes a VIP3A insecticidal toxin, useful in controlling a wide spectrum of lepidopteran insect pests, and a suitable polyadenylation signal. The second cassette comprises a gene which, when expressed, can be used as a selectable marker.

4 Claims, No Drawings

SEQUENCE LISTING

```
<160> NUMBER OF SEQ ID NOS: 25

<210> SEQ ID NO 1
<211> LENGTH: 26
<212> TYPE: DNA
<213> ORGANISM: Artificial Sequence
<220> FEATURE:
<223> OTHER INFORMATION: COT102 nucleotide motif

<400> SEQUENCE: 1

ggcaaatatt caggtaaaca aattga                                26


<210> SEQ ID NO 2
<211> LENGTH: 26
<212> TYPE: DNA
<213> ORGANISM: Artificial Sequence
<220> FEATURE:
<223> OTHER INFORMATION: COT102 nucleotide motif

<400> SEQUENCE: 2

ctatcagtgt ttaataaata tgggca                                26
```

-continued

<210> SEQ ID NO 3
<211> LENGTH: 20
<212> TYPE: DNA
<213> ORGANISM: Artificial Sequence
<220> FEATURE:
<223> OTHER INFORMATION: COT102 nucleotide motif

<400> SEQUENCE: 3
aaggacgtga gcgagatgtt 20

<210> SEQ ID NO 4
<211> LENGTH: 20
<212> TYPE: DNA
<213> ORGANISM: Artificial Sequence
<220> FEATURE:
<223> OTHER INFORMATION: COT102 nucleotide motif

<400> SEQUENCE: 4
tgtgacaccg atccacctaa 20

<210> SEQ ID NO 5
<211> LENGTH: 290
<212> TYPE: DNA
<213> ORGANISM: Artificial Sequence
<220> FEATURE:
<223> OTHER INFORMATION: COT102 nucleotide motif

<400> SEQUENCE: 5
gacaaggaca gcttgagcga ggtgatctac ggcgacatgg acaagctgct gtgtccggac 60
cagagcgagc aaatctacta caccaacaac atcgtgttcc cgaacgagta cgtgatcacc 120
aagatcgact tcaccaagaa gatgaagacc ctgcgctacg aggtgaccgc caacttctac 180
gacagcagca ccggcgagat cgacctgaac aagaagaagg tggagagcag cgaggccgag 240
taccgcaccc tgagcgcgaa cgacgacggc gtctacatgc cactgggcgt 290

<210> SEQ ID NO 6
<211> LENGTH: 347
<212> TYPE: DNA
<213> ORGANISM: Artificial Sequence
<220> FEATURE:
<223> OTHER INFORMATION: COT102 nucleotide motif

<400> SEQUENCE: 6
cgccgtgcac agggtgtcac gttgcaagac ctgcctgaaa ccgaactgcc cgctgttctg 60
cagccggtcg cggaggccat ggatgcgatc gctgcggccg atcttagcca gacgagcggg 120
ttcggcccat tcggaccgca aggaatcggt caatacacta atggcgtgat ttcatatgcg 180
cgattgctga tccccatgtg tatcactggc aaactgtgat ggacgacacc gtcagtgcgt 240
ccgtcgcgca ggctctcgat gagctgatgc tttgggccga ggactgcccc gaagtccggc 300
acctcgtgca cgcggatttc ggctccaaca atgtcctgac ggacaat 347

<210> SEQ ID NO 7
<211> LENGTH: 7474
<212> TYPE: DNA
<213> ORGANISM: Artificial Sequence
<220> FEATURE:
<223> OTHER INFORMATION: COT102 nucleotide motif

<400> SEQUENCE: 7
gtaaacaaat tgacgcttag acaacttaat aacacattgc ggacgttttt aatgtacgcc 60
atgctggccg cccggggtac ccaattcccg atctagtaac atagatgaca ccgcgcgcga 120
taatttatcc tagtttgcgc gctatatttt gttttctatc gcgtattaaa tgtataattg 180

```
cgggactcta atcataaaaa cccatctcat aaataacgtc atgcattaca tgttaattat    240
tacatgctta acgtaattca acagaaatta tatgataatc atcgcaagac cggcaacagg    300
attcaatctt aagaaacttt attgccaaat gtttgaacga tcggggaaat tcggggatcc    360
cggtcggcat ctactctatt cctttgccct cggacgagtg ctggggcgtc ggtttccact    420
atcggcgagt acttctacac agccatcggt ccagacggcc gcgcttctgc gggcgatttg    480
tgtacgcccg acagtcccgg ctccggatcg gacgattgcg tcgcatcgac cctgcgccca    540
agctgcatca tcgaaattgc cgtcaaccaa gctctgatag agttggtcaa gaccaatgcg    600
gagcatatac gcccggagcc gcggcgatcc tgcaagctcc ggatgcctcc gctcgaagta    660
gcgcgtctgc tgctccatac aagccaacca cggcctccag aagaagatgt tggcgacctc    720
gtattgggaa tccccgaaca tcgcctcgct ccagtcaatg accgctgtta tgcggccatt    780
gtccgtcagg acattgttgg agccgaaatc cgcgtgcacg aggtgccgga cttcggggca    840
gtcctcggcc caaagcatca gctcatcgag agcctgcgcg acggacgcac tgacggtgtc    900
gtccatcaca gtttgccagt gatacacatg gggatcagca atcgcgcata tgaaatcacg    960
ccatgtagtg tattgaccga ttccttgcgg tccgaatggg ccgaacccgc tcgtctggct   1020
aagatcggcc gcagcgatcg catccatggc ctccgcgacc ggctgcagaa cagcgggcag   1080
ttcggtttca ggcaggtctt gcaacgtgac accctgtgca cggcgggaga tgcaataggt   1140
caggctctcg ctgaatgccc caatgtcaag cacttccgga atcgggagcg cggccgatgc   1200
aaagtgccga taaacataac gatctttgta gaaaccatcg gcgcagctat ttacccgcag   1260
gacatatcca cgccctccta catcgaagct gaaagcacga gattcttcgc cctccgagag   1320
ctgcatcagg tcggagacgc tgtcgaactt ttcgatcaga aacttctcga cagacgtcgc   1380
ggtgagttca ggctttttca tatcttattg ccccccctaga gtcgagatcc acctgaaata   1440
aaacaataga acaagtagaa accaatcagc gaacatatac caaatcaaaa gccgtaagag   1500
aaatcaaaac aacaccaaag agaaacggat ctaaacataa gaaacctaaa acagagagaa   1560
tcgaacaaag aaaacacaaa aattgaatag atcgtccttg aaaatcctaa tttcacaatc   1620
aagcaagaaa ttacacagat gtaaacacta cgaatcgata tcttagtaat caggacaaaa   1680
tttagaagct ggattgacga aacgaacaat attgtcaaaa gcaatttata caaaagattc   1740
aataatccac ataacaaaaa ttggagatca gatacgaatc aaaaacaaaa agaatcagaa   1800
aatatacctt gaaagagaga gtcgcgagag atttgcagag atcgctttag gctttgggag   1860
agattgaaga gtcagaaaaa gacgaaagga tgaattatta tcttccacac gaaggtcttc   1920
tttatatcgc aaaccaaaag cccaaaaccg tcttttctat taatgagaat aaaatatctt   1980
tagccaaaac aaaaaaagga agatatcagt tgaggattat tatcacgaaa ctaaaggaag   2040
gaatcatatg atacgtgtca tattttccac cgtgcgtttt taaaagaccg actcaagtag   2100
aaacatccta tggtggtggt tggattaggt catccattac atctgcttca ctgacatttt   2160
tctatttttc tttttgtata tacttttcct caaataattt ctttcttttc tatagaagaa   2220
tttaatcaat aaggaaaaag ttcaaaaaag attctttcca ttaagactat gtcttggtta   2280
acccaaccca ttaagaataa gcaatcataa tatatataga gaatactaat actatatatg   2340
agatttttct tttaatttca tgttgattat gatagtttat cttcttgatt taatttatca   2400
atacttggca taaaagattc taatctactc taataaagaa aagaaaaaaa agtatctacc   2460
attgactaat taaaataagg aaacttatct accaaatttg agtatttttt agaacaatct   2520
ttttggttta attccaaaac tctaaaccta attgttggga aaaaggacct aatttttaag   2580
```

aaaagttaat aattagaaga tctgtatgtt ttttttgat ccaagttttt atttcttttc 2640
tcttttttc atgataaaat ctatgttttt ttagtctaca attaaagtaa ttgttattat 2700
tttctttatc ttttttgtt gttgttgtta attccctttt ttttttttaa cagcaacttc 2760
ttaaaaaaaa aaacagttgg gccttgaatt tatttcaggc ctgcgttatt aagcccagat 2820
aataactcaa aacaaaaaaa atgttgaacc ggaataaacc cgcgagatta aatgccggtt 2880
ttcaggtaac atagaagaag aatatatgag gattgaagaa gtattcaaga ggcggaacaa 2940
ttcacaagtc caagagctta aatttctcct cactcttctg ctacagactc ggaactcttt 3000
ctctttgcta aaataagatg ttcaggattt ttgttgcccg acaattcatg tatctcacac 3060
tctctctctt ctctgttctt actactctgt tacattacca ccaactcaag actttcttcc 3120
acaatggcgt ttatgagact tggctccaaa tccggtaccg gagctcgaat tcgaagcttg 3180
catgcctgca gtgatcacca tggtcgacaa aatttagaac gaacttaatt atgatctcaa 3240
atacattgat acatatctca tctagatcta ggttatcatt atgtaagaaa gttttgacga 3300
atatggcacg acaaaatggc tagactcgat gtaattggta tctcaactca acattatact 3360
tataccaaac attagttaga caaaatttaa acaactattt tttatgtatg caagagtcag 3420
catatgtata attgattcag aatcgttttg acgagttcgg atgtagtagt agccattatt 3480
taatgtacat actaatcgtg aatagtgaat atgatgaaac attgtatctt attgtataaa 3540
tatccataaa cacatcatga aagacacttt ctttcacggt ctgaattaat tatgatacaa 3600
ttctaataga aaacgaatta aattacgttg aattgtatga aatctaattg aacaagccaa 3660
ccacgacgac gactaacgtt gcctggattg actcggttta agttaaccac taaaaaaacg 3720
gagctgtcat gtaacacgcg gatcgagcag gtcacagtca tgaagccatc aaagcaaaag 3780
aactaatcca agggctgaga tgattaatta gtttaaaaat tagttaacac gagggaaaag 3840
gctgtctgac agccaggtca cgttatcttt acctgtggtc gaaatgattc gtgtctgtcg 3900
attttaatta tttttttgaa aggccgaaaa taaagttgta agagataaac ccgcctatat 3960
aaattcatat attttcctct ccgctttgaa ttgtctcgtt gtcctcctca ctttcatcag 4020
ccgttttgaa tctccggcga cttgacagag aagaacaagg aagaagacta agagagaaag 4080
taagagataa tccaggagat tcattctccg ttttgaatct tcctcaatct catcttcttc 4140
cgctctttct ttccaaggta ataggaactt tctggatcta ctttatttgc tggatctcga 4200
tcttgttttc tcaatttcct tgagatctgg aattcgttta atttggatct gtgaacctcc 4260
actaaatctt ttggttttac tagaatcgat ctaagttgac cgatcagtta gctcgattat 4320
agctaccaga atttggcttg accttgatgg agagatccat gttcatgtta cctgggaaat 4380
gatttgtata tgtgaattga aatctgaact gttgaagtta gattgaatct gaacactgtc 4440
aatgttagat tgaatctgaa cactgtttaa ggttagatga agtttgtgta tagattcttc 4500
gaaactttag gatttgtagt gtcgtacgtt gaacagaaag ctatttctga ttcaatcagg 4560
gtttatttga ctgtattgaa ctctttttgt gtgtttgcag ctcataaaaa ggatccacca 4620
tgaacaagaa caacaccaag ctgagcaccc gcgccctgcc gagcttcatc gactacttca 4680
acggcatcta cggcttcgcc accggcatca aggacatcat gaacatgatc ttcaagaccg 4740
acaccggcgg cgacctgacc ctggacgaga tcctgaagaa ccagcagctg ctgaacgaca 4800
tcagcggcaa gctggacggc gtgaacggca gcctgaacga cctgatcgcc cagggcaacc 4860
tgaacaccga gctgagcaag gagatcctta agatcgccaa cgagcagaac caggtgctga 4920
acgacgtgaa caacaagctg gacgccatca acaccatgct gcgcgtgtac ctgccgaaga 4980

-continued

```
tcaccagcat gctgagcgac gtgatgaagc agaactacgc cctgagcctg cagatcgagt   5040
acctgagcaa gcagctgcag gagatcagcg acaagctgga catcatcaac gtgaacgtcc   5100
tgatcaacag caccctgacc gagatcaccc cggcctacca gcgcatcaag tacgtgaacg   5160
agaagttcga agagctgacc ttcgccaccg agaccagcag caaggtgaag aaggacggca   5220
gcccggccga catcctggac gagctgaccg agctgaccga gctggcgaag agcgtgacca   5280
agaacgacgt ggacggcttc gagttctacc tgaacacctt ccacgacgtg atggtgggca   5340
acaacctgtt cggccgcagc gccctgaaga ccgccagcga gctgatcacc aaggagaacg   5400
tgaagaccag cggcagcgag gtgggcaacg tgtacaactt cctgatcgtg ctgaccgccc   5460
tgcaggccca ggccttcctg accctgacca cctgtcgcaa gctgctgggc ctggccgaca   5520
tcgactacac cagcatcatg aacgagcact tgaacaagga gaaggaggag ttccgcgtga   5580
acatcctgcc gaccctgagc aacaccttca gcaacccgaa ctacgccaag gtgaagggca   5640
gcgacgagga cgccaagatg atcgtggagg ctaagccggg ccacgcgttg atcggcttcg   5700
agatcagcaa cgacagcatc accgtgctga aggtgtacga ggccaagctg aagcagaact   5760
accaggtgga caaggacagc ttgagcgagg tgatctacgg cgacatggac aagctgctgt   5820
gtccggacca gagcgagcaa atctactaca ccaacaacat cgtgttcccg aacgagtacg   5880
tgatcaccaa gatcgacttc accaagaaga tgaagaccct gcgctacgag gtgaccgcca   5940
acttctacga cagcagcacc ggcgagatcg acctgaacaa gaagaaggtg gagagcagcg   6000
aggccgagta ccgcaccctg agcgcgaacg acgacggcgt ctacatgcca ctgggcgtga   6060
tcagcgagac cttcctgacc ccgatcaacg gctttggcct gcaggccgac gagaacagcc   6120
gcctgatcac cctgacctgt aagagctacc tgcgcgagct gctgctagcc accgacctga   6180
gcaacaagga gaccaagctg atcgtgccac cgagcggctt catcagcaac atcgtggaga   6240
acggcagcat cgaggaggac aacctggagc cgtggaaggc caacaacaag aacgcctacg   6300
tggaccacac cggcggcgtg aacggcacca aggccctgta cgtgcacaag gacggcggca   6360
tcagccagtt catcggcgac aagctgaagc cgaagaccga gtacgtgatc cagtacaccg   6420
tgaagggcaa gccatcgatt cacctgaagg acgagaacac cggctacatc cactacgagg   6480
acaccaacaa caacctggag gactaccaga ccatcaacaa gcgcttcacc accggcaccg   6540
acctgaaggg cgtgtacctg atcctgaaga gccagaacgg cgacgaggcc tggggcgaca   6600
acttcatcat cctggagatc agcccgagcg agaagctgct gagcccggag ctgatcaaca   6660
ccaacaactg gaccagcacc ggcagcacca acatcagcgg caacaccctg accctgtacc   6720
agggcggccg cggcatcctg aagcagaacc tgcagctgga cagcttcagc acctaccgcg   6780
tgtacttcag cgtgagcggc gacgccaacg tgcgcatccg caactcccgc gaggtgctgt   6840
tcgagaagag gtacatgagc ggcgccaagg acgtgagcga gatgttcacc accaagttcg   6900
agaaggacaa cttctacatc gagctgagcc agggcaacaa cctgtacggc ggcccgatcg   6960
tgcacttcta cgacgtgagc atcaagtagg agctctagat ccccgaattt ccccgatcgt   7020
tcaaacattt ggcaataaag tttcttaaga ttgaatcctg ttgccggtct tgcgatgatt   7080
atcatataat ttctgttgaa ttacgttaag catgtaataa ttaacatgta atgcatgacg   7140
ttatttatga gatgggtttt tatgattaga gtcccgcaat tatacattta atacgcgata   7200
gaaaacaaaa tatagcgcgc aaactaggat aaattatcgc gcgcggtgtc atctatgtta   7260
ctagatcggg aattgggtac cgagctcgaa ttcggcgcgc ccaattgatt taaatggccg   7320
ctgcggccaa ttcctgcagc gttgcggttc tgtcagttcc aaacgtaaaa cggcttgtcc   7380
```

cgcgtcatcg gcgggggtca taacgtgact cccttaattc tccgctcatg atcagattgt 7440
cgtttcccgc cttcagttta aactatcagt gttt 7474

<210> SEQ ID NO 8
<211> LENGTH: 789
<212> TYPE: PRT
<213> ORGANISM: Artificial Sequence
<220> FEATURE:
<223> OTHER INFORMATION: VIP3A protein motif

<400> SEQUENCE: 8

Met Asn Lys Asn Asn Thr Lys Leu Ser Thr Arg Ala Leu Pro Ser Phe
1 5 10 15

Ile Asp Tyr Phe Asn Gly Ile Tyr Gly Phe Ala Thr Gly Ile Lys Asp
20 25 30

Ile Met Asn Met Ile Phe Lys Thr Asp Thr Gly Gly Asp Leu Thr Leu
35 40 45

Asp Glu Ile Leu Lys Asn Gln Gln Leu Leu Asn Asp Ile Ser Gly Lys
50 55 60

Leu Asp Gly Val Asn Gly Ser Leu Asn Asp Leu Ile Ala Gln Gly Asn
65 70 75 80

Leu Asn Thr Glu Leu Ser Lys Glu Ile Leu Lys Ile Ala Asn Glu Gln
85 90 95

Asn Gln Val Leu Asn Asp Val Asn Asn Lys Leu Asp Ala Ile Asn Thr
100 105 110

Met Leu Arg Val Tyr Leu Pro Lys Ile Thr Ser Met Leu Ser Asp Val
115 120 125

Met Lys Gln Asn Tyr Ala Leu Ser Leu Gln Ile Glu Tyr Leu Ser Lys
130 135 140

Gln Leu Gln Glu Ile Ser Asp Lys Leu Asp Ile Ile Asn Val Asn Val
145 150 155 160

Leu Ile Asn Ser Thr Leu Thr Glu Ile Thr Pro Ala Tyr Gln Arg Ile
165 170 175

Lys Tyr Val Asn Glu Lys Phe Glu Glu Leu Thr Phe Ala Thr Glu Thr
180 185 190

Ser Ser Lys Val Lys Lys Asp Gly Ser Pro Ala Asp Ile Leu Asp Glu
195 200 205

Leu Thr Glu Leu Thr Glu Leu Ala Lys Ser Val Thr Lys Asn Asp Val
210 215 220

Asp Gly Phe Glu Phe Tyr Leu Asn Thr Phe His Asp Val Met Val Gly
225 230 235 240

Asn Asn Leu Phe Gly Arg Ser Ala Leu Lys Thr Ala Ser Glu Leu Ile
245 250 255

Thr Lys Glu Asn Val Lys Thr Ser Gly Ser Glu Val Gly Asn Val Tyr
260 265 270

Asn Phe Leu Ile Val Leu Thr Ala Leu Gln Ala Gln Ala Phe Leu Thr
275 280 285

Leu Thr Thr Cys Arg Lys Leu Leu Gly Leu Ala Asp Ile Asp Tyr Thr
290 295 300

Ser Ile Met Asn Glu His Leu Asn Lys Glu Lys Glu Glu Phe Arg Val
305 310 315 320

Asn Ile Leu Pro Thr Leu Ser Asn Thr Phe Ser Asn Pro Asn Tyr Ala
325 330 335

Lys Val Lys Gly Ser Asp Glu Asp Ala Lys Met Ile Val Glu Ala Lys
340 345 350

-continued

```
Pro Gly His Ala Leu Ile Gly Phe Glu Ile Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
            420                 425                 430

Thr Leu Arg Tyr Glu Val Thr Ala Asn Phe Tyr Asp Ser Ser Thr Gly
        435                 440                 445

Glu Ile Asp Leu Asn Lys Lys Lys Val Glu Ser Ser Glu Ala Glu Tyr
    450                 455                 460

Arg Thr Leu Ser Ala Asn Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Ser Ile
    530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
        595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
```

-continued 770 775 780

Asp Val Ser Ile Lys
785

<210> SEQ ID NO 9
<211> LENGTH: 20
<212> TYPE: DNA
<213> ORGANISM: Artificial Sequence
<220> FEATURE:
<223> OTHER INFORMATION: COT102 nucleotide motif

<400> SEQUENCE: 9
ggtccctgga tacggtgtca 20

<210> SEQ ID NO 10
<211> LENGTH: 20
<212> TYPE: DNA
<213> ORGANISM: Artificial Sequence
<220> FEATURE:
<223> OTHER INFORMATION: COT102 nucleotide motif

<400> SEQUENCE: 10
ttgagggttg gatcctttgc 20

<210> SEQ ID NO 11
<211> LENGTH: 27
<212> TYPE: DNA
<213> ORGANISM: Artificial Sequence
<220> FEATURE:
<223> OTHER INFORMATION: COT102 nucleotide motif
<220> FEATURE:
<221> NAME/KEY: modified_base
<222> LOCATION: (1)..(1)
<223> OTHER INFORMATION: TET label at 5' end
<220> FEATURE:
<221> NAME/KEY: modified_base
<222> LOCATION: (27)..(27)
<223> OTHER INFORMATION: TAMRA label at 3' end

<400> SEQUENCE: 11
ccaacatcat caatggtggc atcgaat 27

<210> SEQ ID NO 12
<211> LENGTH: 19
<212> TYPE: DNA
<213> ORGANISM: Artificial Sequence
<220> FEATURE:
<223> OTHER INFORMATION: COT102 nucleotide motif

<400> SEQUENCE: 12
caggcaggtc ttgcaacgt 19

<210> SEQ ID NO 13
<211> LENGTH: 21
<212> TYPE: DNA
<213> ORGANISM: Artificial Sequence
<220> FEATURE:
<223> OTHER INFORMATION: COT102 nucleotide motif

<400> SEQUENCE: 13
cgagagcctg acctattgca t 21

<210> SEQ ID NO 14
<211> LENGTH: 19
<212> TYPE: DNA
<213> ORGANISM: Artificial Sequence
<220> FEATURE:
<223> OTHER INFORMATION: COT102 nucleotide motif
<220> FEATURE:
<221> NAME/KEY: modified_base
<222> LOCATION: (1)..(1)
<223> OTHER INFORMATION: FAM label at 5' end
<220> FEATURE:
<221> NAME/KEY: modified_base
<222> LOCATION: (19)..(19)
<223> OTHER INFORMATION: TAMRA label at 3' end

<400> SEQUENCE: 14
acaccctgtg cacggcggg 19

<210> SEQ ID NO 15
<211> LENGTH: 20
<212> TYPE: DNA
<213> ORGANISM: Artificial Sequence
<220> FEATURE:
<223> OTHER INFORMATION: COT102 nucleotide motif

<400> SEQUENCE: 15
atgaagaccc tgcgctacga 20

<210> SEQ ID NO 16
<211> LENGTH: 19
<212> TYPE: DNA
<213> ORGANISM: Artificial Sequence
<220> FEATURE:
<223> OTHER INFORMATION: COT102 nucleotide motif

<400> SEQUENCE: 16
acgcccagtg gcatgtaga 19

<210> SEQ ID NO 17
<211> LENGTH: 21
<212> TYPE: DNA
<213> ORGANISM: Artificial Sequence
<220> FEATURE:
<223> OTHER INFORMATION: COT102 nucleotide motif
<220> FEATURE:
<221> NAME/KEY: modified_base
<222> LOCATION: (1)..(1)
<223> OTHER INFORMATION: FAM label at 5' end
<220> FEATURE:
<221> NAME/KEY: modified_base
<222> LOCATION: (21)..(21)
<223> OTHER INFORMATION: TAMRA label at 3' end

<400> SEQUENCE: 17
agcgaggccg agtaccgcac c 21

<210> SEQ ID NO 18
<211> LENGTH: 19
<212> TYPE: DNA
<213> ORGANISM: Artificial Sequence
<220> FEATURE:
<223> OTHER INFORMATION: COT102 nucleotide motif

<400> SEQUENCE: 18
ccaacctatt cttcctctc 19

<210> SEQ ID NO 19
<211> LENGTH: 19
<212> TYPE: DNA
<213> ORGANISM: Artificial Sequence
<220> FEATURE:
<223> OTHER INFORMATION: COT102 nucleotide motif

<400> SEQUENCE: 19
gtatatgctc cgcattggt 19

<210> SEQ ID NO 20
<211> LENGTH: 19
<212> TYPE: DNA
<213> ORGANISM: Artificial Sequence
<220> FEATURE:
<223> OTHER INFORMATION: COT102 nucleotide motif

<400> SEQUENCE: 20
gtgttgcatt agaagatgt 19

<210> SEQ ID NO 21
<211> LENGTH: 9356
<212> TYPE: DNA
<213> ORGANISM: Artificial Sequence
<220> FEATURE:
<223> OTHER INFORMATION: COT102 nucleotide motif

<400> SEQUENCE: 21
ctatagggca cgcgtggtcg acggcccggg ctggtgtcga aactactttg taatatacaa 60
ccaccttttc agttaaattg catccctaat tctagccatg ccatgcattt agatattacc 120
tgaatatttc aatcaaaatc catttccaaa tcatgtaagt accagcacac aaacaattcc 180
aactaagttc attgatgagc tccactcaac tattttaaag aaaatctacc ccaatcctta 240
ctgatgagtg aaagcaccta gcagtgtgaa aagaaaacca aatatgcatt gatccatgga 300
cagactaata tgcaacacct tagcactaga taaaatgcaa gacttttcac tctaaatatg 360
accatgttct tctagttaaa attgatgtta attgaaccca gtgtctctta ctttcgattc 420
tattagaaaa cacacaacaa tgccatacaa actgcatttt tccttgaaaa aagaaaatca 480
aacagcaatt gtataaggaa agtggcctta aatatatatt aactgaagat taaatgaaaa 540
cagccaagtg ttcaagtaat tggaaacagc tattccctga ccttaaatat ataaaaaaac 600
tgtagattaa aggatatcaa cctcatttaa cactcaagat caaacttacc agtaaacaga 660
gagtaggctt cccctaacat acctatatct tgacagttca gaaaattaca gcataacttt 720
ttcacattgt cctaatcaaa tttctaaata catcaaactt tggcaactta gaacaaacct 780
aataaactgc tccaacttgg gcatggacag caaatgtaga tatggacaac tttgacccaa 840
aattcaaaga taaaggtcca aaagtggaac cactactagg gtcttttagt cgtaagtgtg 900
gagctgcctt atcctaagtt tcccaaaccc ttttatgctt catttgaggt tagaatctcg 960
ggaaggcagg tcttttacaa gcgttagcac aatttagttg catcattgtt ggtgccaaac 1020
catttttttc tcaaccaacc tattcttcct ctctgtttta aggtactatt cacagaagaa 1080
gataggtagt ttttaaggag aattactatc caacattagc aaatagaaac ccaactatct 1140
gctggcttca aaatgtagcg acagactaat accaaacaaa accatgagat tgtagagaga 1200
taccttgggt ttgatatgaa tggccgacgt cctcaaaaga gaaatcttcg ttttctacat 1260
aattaacaat gccaaagcaa aagatgagta atttggattt tttgaaaaat aaaccaataa 1320
tacaattcaa atatgaaact ttgaaagaaa acactcattg taagatcaaa aaaggcaaat 1380
attcaggtaa acaaattgac gcttagacaa cttaataaca cattgcggac gtttttaatg 1440
tacgccatgc tggccgcccg gggtacccaa ttcccgatct agtaacatag atgacaccgc 1500
gcgcgataat ttatcctagt ttgcgcgcta tattttgttt tctatcgcgt attaaatgta 1560
taattgcggg actctaatca taaaaaccca tctcataaat aacgtcatgc attacatgtt 1620
aattattaca tgcttaacgt aattcaacag aaattatatg ataatcatcg caagaccggc 1680
aacaggattc aatcttaaga aactttattg ccaaatgttt gaacgatcgg ggaaattcgg 1740

```
ggatcccggt cggcatctac tctattcctt tgccctcgga cgagtgctgg ggcgtcggtt   1800
tccactatcg gcgagtactt ctacacagcc atcggtccag acggccgcgc ttctgcgggc   1860
gatttgtgta cgcccgacag tcccggctcc ggatcggacg attgcgtcgc atcgaccctg   1920
cgcccaagct gcatcatcga aattgccgtc aaccaagctc tgatagagtt ggtcaagacc   1980
aatgcggagc atatacgccc ggagccgcgg cgatcctgca agctccggat gcctccgctc   2040
gaagtagcgc gtctgctgct ccatacaagc caaccacggc ctccagaaga agatgttggc   2100
gacctcgtat tgggaatccc cgaacatcgc ctcgctccag tcaatgaccg ctgttatgcg   2160
gccattgtcc gtcaggacat tgttggagcc gaaatccgcg tgcacgaggt gccggacttc   2220
ggggcagtcc tcggcccaaa gcatcagctc atcgagagcc tgcgcgacgg acgcactgac   2280
ggtgtcgtcc atcacagttt gccagtgata cacatgggga tcagcaatcg cgcatatgaa   2340
atcacgccat gtagtgtatt gaccgattcc ttgcggtccg aatgggccga acccgctcgt   2400
ctggctaaga tcggccgcag cgatcgcatc catggcctcc gcgaccggct gcagaacagc   2460
gggcagttcg gtttcaggca ggtcttgcaa cgtgacaccc tgtgcacggc gggagatgca   2520
ataggtcagg ctctcgctga atgccccaat gtcaagcact tccggaatcg ggagcgcggc   2580
cgatgcaaag tgccgataaa cataacgatc tttgtagaaa ccatcggcgc agctatttac   2640
ccgcaggaca tatccacgcc ctcctacatc gaagctgaaa gcacgagatt cttcgccctc   2700
cgagagctgc atcaggtcgg agacgctgtc gaacttttcg atcagaaact tctcgacaga   2760
cgtcgcggtg agttcaggct tttcatatc ttattgcccc cctagagtcg agatccacct    2820
gaaataaaac aatagaacaa gtagaaacca atcagcgaac atataccaaa tcaaaagccg   2880
taagagaaat caaaacaaca ccaaagagaa acggatctaa acataagaaa cctaaaacag   2940
agagaatcga acaaagaaaa cacaaaaatt gaatagatcg tccttgaaaa tcctaatttc   3000
acaatcaagc aagaaattac acagatgtaa acactacgaa tcgatatctt agtaatcagg   3060
acaaaattta gaagctggat tgacgaaacg aacaatattg tcaaaagcaa tttatacaaa   3120
agattcaata atccacataa caaaaattgg agatcagata cgaatcaaaa acaaaaagaa   3180
tcagaaaata taccttgaaa gagagagtcg cgagagattt gcagagatcg ctttaggctt   3240
tgggagagat tgaagagtca gaaaaagacg aaaggatgaa ttattatctt ccacacgaag   3300
gtcttcttta tatcgcaaac caaaagccca aaaccgtctt ttctattaat gagaataaaa   3360
tatctttagc caaaacaaaa aaaggaagat atcagttgag gattattatc acgaaactaa   3420
aggaaggaat catatgatac gtgtcatatt ttccaccgtg cgtttttaaa agaccgactc   3480
aagtagaaac atcctatggt ggtggttgga ttaggtcatc cattacatct gcttcactga   3540
catttttcta tttttctttt tgtatatact tttcctcaaa taatttcttt cttttctata   3600
gaagaattta atcaataagg aaaaagttca aaaaagattc tttccattaa gactatgtct   3660
tggttaaccc aacccattaa gaataagcaa tcataatata tatagagaat actaatacta   3720
tatatgagat ttttctttta atttcatgtt gattatgata gtttatcttc ttgatttaat   3780
ttatcaatac ttggcataaa agattctaat ctactctaat aaagaaaaga aaaaaaagta   3840
tctaccattg actaattaaa ataaggaaac ttatctacca aatttgagta ttttttagaa   3900
caatcttttt ggtttaattc caaaactcta aacctaattg ttgggaaaaa ggacctaatt   3960
tttaagaaaa gttaataatt agaagatctg tatgtttttt tttgatccaa gtttttattt   4020
cttttctctt tttttcatga taaaatctat gtttttttag tctacaatta aagtaattgt   4080
tattatttc tttatctttt tttgttgttg ttgttaattc cctttttttt ttttaacagc    4140
```

-continued

```
aacttcttaa aaaaaaaaac agttgggcct tgaatttatt tcaggcctgc gttattaagc   4200
ccagataata actcaaaaca aaaaaaatgt tgaaccggaa taaacccgcg agattaaatg   4260
ccggttttca ggtaacatag aagaagaata tatgaggatt gaagaagtat tcaagaggcg   4320
gaacaattca caagtccaag agcttaaatt tctcctcact cttctgctac agactcggaa   4380
ctctttctct ttgctaaaat aagatgttca ggatttttgt tgcccgacaa ttcatgtatc   4440
tcacactctc tctcttctct gttcttacta ctctgttaca ttaccaccaa ctcaagactt   4500
tcttccacaa tggcgtttat gagacttggc tccaaatccg gtaccggagc tcgaattcga   4560
agcttgcatg cctgcagtga tcaccatggt cgacaaaatt tagaacgaac ttaattatga   4620
tctcaaatac attgatacat atctcatcta gatctaggtt atcattatgt aagaaagttt   4680
tgacgaatat ggcacgacaa aatggctaga ctcgatgtaa ttggtatctc aactcaacat   4740
tatacttata ccaaacatta gttagacaaa atttaaacaa ctatttttta tgtatgcaag   4800
agtcagcata tgtataattg attcagaatc gttttgacga gttcggatgt agtagtagcc   4860
attatttaat gtacatacta atcgtgaata gtgaatatga tgaaacattg tatcttattg   4920
tataaatatc cataaacaca tcatgaaaga cactttcttt cacggtctga attaattatg   4980
atacaattct aatagaaaac gaattaaatt acgttgaatt gtatgaaatc taattgaaca   5040
agccaaccac gacgacgact aacgttgcct ggattgactc ggtttaagtt aaccactaaa   5100
aaaacggagc tgtcatgtaa cacgcggatc gagcaggtca cagtcatgaa gccatcaaag   5160
caaaagaact aatccaaggg ctgagatgat taattagttt aaaaattagt taacacgagg   5220
gaaaaggctg tctgacagcc aggtcacgtt atctttacct gtggtcgaaa tgattcgtgt   5280
ctgtcgattt taattatttt tttgaaaggc cgaaaataaa gttgtaagag ataaacccgc   5340
ctatataaat tcatatattt tcctctccgc tttgaattgt ctcgttgtcc tcctcacttt   5400
catcagccgt tttgaatctc cggcgacttg acagagaaga acaaggaaga agactaagag   5460
agaaagtaag agataatcca ggagattcat tctccgtttt gaatcttcct caatctcatc   5520
ttcttccgct ctttctttcc aaggtaatag gaactttctg gatctacttt atttgctgga   5580
tctcgatctt gttttctcaa tttccttgag atctggaatt cgtttaattt ggatctgtga   5640
acctccacta aatcttttgg ttttactaga atcgatctaa gttgaccgat cagttagctc   5700
gattatagct accagaattt ggcttgacct tgatggagag atccatgttc atgttacctg   5760
ggaaatgatt tgtatatgtg aattgaaatc tgaactgttg aagttagatt gaatctgaac   5820
actgtcaatg ttagattgaa tctgaacact gtttaaggtt agatgaagtt tgtgtataga   5880
ttcttcgaaa ctttaggatt tgtagtgtcg tacgttgaac agaaagctat ttctgattca   5940
atcagggttt atttgactgt attgaactct ttttgtgtgt ttgcagctca taaaaaggat   6000
ccaccatgaa caagaacaac accaagctga gcacccgcgc cctgccgagc ttcatcgact   6060
acttcaacgg catctacggc ttcgccaccg gcatcaagga catcatgaac atgatcttca   6120
agaccgacac cggcggcgac ctgaccctgg acgagatcct gaagaaccag cagctgctga   6180
acgacatcag cggcaagctg gacggcgtga acggcagcct gaacgacctg atcgcccagg   6240
gcaacctgaa caccgagctg agcaaggaga tccttaagat cgccaacgag cagaaccagg   6300
tgctgaacga cgtgaacaac aagctggacg ccatcaacac catgctgcgc gtgtacctgc   6360
cgaagatcac cagcatgctg agcgacgtga tgaagcagaa ctacgccctg agcctgcaga   6420
tcgagtacct gagcaagcag ctgcaggaga tcagcgacaa gctggacatc atcaacgtga   6480
acgtcctgat caacagcacc ctgaccgaga tcaccccggc ctaccagcgc atcaagtacg   6540
```

tgaacgagaa gttcgaagag ctgaccttcg ccaccgagac cagcagcaag gtgaagaagg 6600
acggcagccc ggccgacatc ctggacgagc tgaccgagct gaccgagctg gcgaagagcg 6660
tgaccaagaa cgacgtggac ggcttcgagt tctacctgaa caccttccac gacgtgatgg 6720
tgggcaacaa cctgttcggc cgcagcgccc tgaagaccgc cagcgagctg atcaccaagg 6780
agaacgtgaa gaccagcggc agcgaggtgg gcaacgtgta caacttcctg atcgtgctga 6840
ccgccctgca ggcccaggcc ttcctgaccc tgaccacctg tcgcaagctg ctgggcctgg 6900
ccgacatcga ctacaccagc atcatgaacg agcacttgaa caaggagaag gaggagttcc 6960
gcgtgaacat cctgccgacc ctgagcaaca ccttcagcaa cccgaactac gccaaggtga 7020
agggcagcga cgaggacgcc aagatgatcg tggaggctaa gccgggccac gcgttgatcg 7080
gcttcgagat cagcaacgac agcatcaccg tgctgaaggt gtacgaggcc aagctgaagc 7140
agaactacca ggtggacaag gacagcttga gcgaggtgat ctacggcgac atggacaagc 7200
tgctgtgtcc ggaccagagc gagcaaatct actacaccaa caacatcgtg ttcccgaacg 7260
agtacgtgat caccaagatc gacttcacca agaagatgaa gaccctgcgc tacgaggtga 7320
ccgccaactt ctacgacagc agcaccggcg agatcgacct gaacaagaag aaggtggaga 7380
gcagcgaggc cgagtaccgc accctgagcg cgaacgacga cggcgtctac atgccactgg 7440
gcgtgatcag cgagaccttc ctgaccccga tcaacggctt tggcctgcag gccgacgaga 7500
acagccgcct gatcaccctg acctgtaaga gctacctgcg cgagctgctg ctagccaccg 7560
acctgagcaa caaggagacc aagctgatcg tgccaccgag cggcttcatc agcaacatcg 7620
tggagaacgg cagcatcgag gaggacaacc tggagccgtg gaaggccaac aacaagaacg 7680
cctacgtgga ccacaccggc ggcgtgaacg gcaccaaggc cctgtacgtg cacaaggacg 7740
gcggcatcag ccagttcatc ggcgacaagc tgaagccgaa gaccgagtac gtgatccagt 7800
acaccgtgaa gggcaagcca tcgattcacc tgaaggacga gaacaccggc tacatccact 7860
acgaggacac caacaacaac ctggaggact accagaccat caacaagcgc ttcaccaccg 7920
gcaccgacct gaagggcgtg tacctgatcc tgaagagcca gaacggcgac gaggcctggg 7980
gcgacaactt catcatcctg gagatcagcc cgagcgagaa gctgctgagc ccggagctga 8040
tcaacaccaa caactggacc agcaccggca gcaccaacat cagcggcaac accctgaccc 8100
tgtaccaggg cggccgcggc atcctgaagc agaacctgca gctggacagc ttcagcacct 8160
accgcgtgta cttcagcgtg agcggcgacg ccaacgtgcg catccgcaac tcccgcgagg 8220
tgctgttcga gaagaggtac atgagcggcg ccaaggacgt gagcgagatg ttcaccacca 8280
agttcgagaa ggacaacttc tacatcgagc tgagccaggg caacaacctg tacggcggcc 8340
cgatcgtgca cttctacgac gtgagcatca agtaggagct ctagatcccc gaatttcccc 8400
gatcgttcaa acatttggca ataaagtttc ttaagattga atcctgttgc cggtcttgcg 8460
atgattatca tataatttct gttgaattac gttaagcatg taataattaa catgtaatgc 8520
atgacgttat ttatgagatg ggtttttatg attagagtcc cgcaattata catttaatac 8580
gcgatagaaa acaaaatata gcgcgcaaac taggataaat tatcgcgcgc ggtgtcatct 8640
atgttactag atcgggaatt gggtaccgag ctcgaattcg gcgcgcccaa ttgatttaaa 8700
tggccgctgc ggccaattcc tgcagcgttg cggttctgtc agttccaaac gtaaaacggc 8760
ttgtcccgcg tcatcggcgg gggtcataac gtgactccct taattctccg ctcatgatca 8820
gattgtcgtt tcccgccttc agtttaaact atcagtgttt aataaatatg ggcaatcttt 8880
ccctacaccg actgtactgt tactgtaata gactccggcc tagactgatt ctgaattctg 8940

```
tctgtttact gactgttact ctagtaaggg gattacacac tgagttttag taaactcacc   9000

ccgtttatta actgtgcagg taatccccaa cattaggtgg atcggtgtca cagaaggact   9060

cggagacgac cacacaactg cacatgtttt tttatttcgt ttatttagtc aagcactttg   9120

gtttttgatt tgggttgtat taaggcctct ttattttctt aaccttttat ttgggaaatt   9180

tatttagtat gcttaatata tgttagaagt agggcacggt tttccaaaac aacaattggc   9240

tttcaaaata tctcgtttcc gtaactgttt aaaagtatgc ttctgcagca aataaggttt   9300

taagggaatt aacgtttcac aagttttaaa tggctagagg ttttgagtag taagaa       9356


<210> SEQ ID NO 22
<211> LENGTH: 20
<212> TYPE: DNA
<213> ORGANISM: Artificial Sequence
<220> FEATURE:
<223> OTHER INFORMATION: COT102 nucleotide motif

<400> SEQUENCE: 22

gatcggggtc aggaaggtct                                                  20


<210> SEQ ID NO 23
<211> LENGTH: 20
<212> TYPE: DNA
<213> ORGANISM: Artificial Sequence
<220> FEATURE:
<223> OTHER INFORMATION: COT102 nucleotide motif

<400> SEQUENCE: 23

cagcatcatg aacgagcact                                                  20


<210> SEQ ID NO 24
<211> LENGTH: 20
<212> TYPE: DNA
<213> ORGANISM: Artificial Sequence
<220> FEATURE:
<223> OTHER INFORMATION: COT102 nucleotide motif

<400> SEQUENCE: 24

cagcgagagc ctgacctatt                                                  20


<210> SEQ ID NO 25
<211> LENGTH: 20
<212> TYPE: DNA
<213> ORGANISM: Artificial Sequence
<220> FEATURE:
<223> OTHER INFORMATION: COT102 nucleotide motif

<400> SEQUENCE: 25

caggacattg ttggagccga                                                  20
```

COT102 INSECTICIDAL COTTON

This is divisional of U.S. patent application Ser. No. 11/853,243, filed Sep. 11, 2007, now U.S. Pat. No. 7,803,547 which is a divisional of U.S. patent application Ser. No. 10/530,234 filed Sep. 29, 2005, now U.S. Pat. No. 7,371,940 B2, which is a §371 of PCT/EP2003/011725, filed Oct. 23, 2003, and published May 13, 2004 as WO 2004/039986, which claims priority of GB0225129.6, filed Oct. 29, 2002. These documents are incorporated herein in their entirety.

The present invention relates to genetic engineering of plants and in particular to an insect in resistant transgenic cotton plant. It also relates to methods of detecting material derived from the plant.

Plant pests are a major factor in the loss of the world's important agricultural crops. About $8 billion is lost every year in the U.S. due to infestations of plants by non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Good control of insect pests can thus be reached, but these chemicals can sometimes also affect other, beneficial insects. Another problem resulting from the wide use of chemical pesticides is the appearance of resistant insect varieties. This has been partially alleviated by various resistance management practices, but there is an increasing need for alternative pest control agents. Biological pest control agents, such as *Bacillus thuringiensis* strains expressing pesticidal toxins like δ-endotoxins, have also been applied to crop plants with satisfactory results, offering an alternative or compliment to chemical pesticides. The genes coding for some of these δ-endotoxins have been isolated and their expression in heterologous hosts has been shown to provide another tool for the control of economically important insect pests. In particular, the expression of insecticidal toxins such as *Bacillus thuringiensis* δ-endotoxins in transgenic plants, has provided efficient protection against selected insect pests, and transgenic plants expressing such toxins have been commercialised, allowing farmers to reduce applications of chemical insect control agents.

Recently, a new family of insecticidal proteins produced by *Bacillus* sp. during the vegetative stages of growth (vegetative insecticidal proteins (VIPs)) has been identified. U.S. Pat. Nos. 5,877,012, 6,107,279, and 6,137,033 describe vip3A toxin genes isolated from *Bacillus* species. The VIP3A toxins possess insecticidal activity against a wide spectrum of lepidopteran insects including but not limited to fall armyworm, *Spodoptera frugiperda*, black cutworm, *Agrotis ipsilon*, sugarcane borer, *Diatraea saccharalis*, and lesser cornstalk borer, *Elasmopalpus lignosellus*, and when expressed in transgenic plants, for example cotton, confer protection on the plant from insect feeding damage.

The cotton family, genus *Gossypium*, a member of the Malvaceae, consists of 39 species, of which *Gossypium hirsutum* is the most commonly cultivated species. Three other species are also cultivated: *G. arboreum, G. barbadense*, and *G. herbaceum*. These cultivated species are grown primarily for the seed hairs that are made into textiles. Cotton is suitable as a textile fibre because the mature dry hairs twist in such a way that fine strong threads can be spun from them. Other products, such as cottonseed oil, cake, and cotton linters are by-products of fibre production.

Damage to cotton crops by insect pests throughout the world results in a significant yield loss each year. Effective control of these pests to minimise yield loss is of great economic importance. Examples of insect pests of cotton include Beet armyworm (*Spodoptera exigua*), Boll weevil (*Anthonomus grandis grandis*), Cabbage looper (*Trichoplusia ni*), Clouded plant bug (*Neurocolpus nubilus*), Cotton aphid (*Aphis gossypii*), Cotton bollworm (*Heliocoverpa zea*), Cutworms (*Feltia subterranea, Peridroma saucia, Agrotis ipsilon*), European corn borer (*Ostrinia nubilalis*), Fall armyworm (*Spodoptera frugiperda*), Seedling thrips (*Frankliniella* spp.), Soybean looper (*Pseudoplusia includens*), Stink bugs (*Nezara viridula, Acrosternum hilare, Euschisius servus*), Tarnished plant bug (*Lygus lineolaris*), Tobacco budworm (*Heliothis virescens*) and Whiteflies (*Trialeurodes abutilonea, Bemisia tabaci*).

Transformation and regeneration of cotton plants is now a well-established procedure, typically based on *Agrobacterium tumefaciens* mediated transfer of foreign DNA into cotton plant parts and regeneration of said plant parts in tissue culture into fully fertile, transgenic cotton plants.

There exists a requirement to generate a cotton plant that is insect resistant so that yield loss through damage to cotton crops by insect pests is reduced. An insect resistant cotton plant could reduce the need to apply chemical pesticides, which may be detrimental to other, beneficial insects and the environment.

Therefore, the present invention relates to an insect resistant transgenic cotton event, designated COT102. It also relates to methods of detecting plant material derived therefrom. "COT102 event" in the context of this application refers to the original insecticidal transgenic cotton plant described herein. "Insecticidal" as used herein refers to any inhibitory effect on an insect, including but not limited to reduced feeding, retarded growth, reduced fecundity, paralysis or death. "Fecundity" comprises all aspects related to reproduction such as reproductive ability, reproductive frequency and number of offspring. Also embraced by this invention is any plant material derived from the COT102 event, including seeds.

The COT102 event exhibits a novel genotype comprising two expression cassettes. The first cassette comprises a suitable promoter for expression in plants operably linked to a gene that encodes a VIP3A insecticidal toxin, useful in controlling a wide spectrum of lepidopteran insect pests, and a suitable polyadenylation signal. Suitable promoters may be isolated from, inter alia, plants. Numerous plant promoters have been isolated and characterised including constitutive, switchable and/or tissue specific promoters. Suitable promoters may be selected from the following, non-limiting group: CaMV35S, FMV35S, Ubiquitin, Act2, NOS, OCS, Cestrum yellow leaf curl virus promoter, Patatin, E9, alcA/alcR switch, GST switch, RMS switch, oleosin, Gelvin, ribulose bisphosphate carboxylase-oxygenase small sub-unit, actin 7, MR7 promoter (maize), Gos 9 (rice), GOS2 promoters, MasOcs (or super promoter), RolD promoter (*Agrobacterium rhizogenes*), SuperMAS promoter, and Suc2 promoter (*Arabidopsis*). In one embodiment of the present invention, the promoter is the Actin promoter, Act2, from *Arabidopsis*. Additional elements such as enhancer sequences may also be incorporated into the expression cassette in order to boost levels of gene expression, for example transcriptional or translational enhancers, such as tobacco etch virus (TEV) translation activator, CaMV35S enhancer, and FMV35S enhancer. Alternatively it may be desirable to include a targeting sequence, for example, to direct transportation of the VIP3A toxin to a particular cellular compartment. For example if it is desired to provide the protein outside of the cell then an extracellular targeting sequence may be ligated to the polynucleotide encoding the VIP protein. Other examples of targeting include targeting to a specific intracellular organelle or compartment, for example to the endoplasmic reticulum using a 'KDEL' retention sequence. Numerous polyadenylation signals have been isolated and characterised. Examples of suitable polyadenylation signals functional in plants include that from the nopaline synthase gene (nos) of *Agrobacterium tumefaciens*, from the proteinase inhibitor II gene and from the alpha-tubulin gene (EP-A 652,286). In one embodiment of the present invention, the polyadenylation signal is that from the nos gene of *Agrobacterium tumefaciens*.

According to the invention, the polynucleotide encoding the VIP3A protein may also be codon-optimised or otherwise altered to enhance for example, transcription once it is incorporated into plant material. Such codon optimisation may also be used to alter the predicted secondary structure of the RNA transcript produced in any transformed cell, or to destroy cryptic RNA instability elements present in the unaltered transcript, thereby increasing the stability and/or availability of the transcript in the transformed cell (Abler and Green (1996) Plant Molecular Biology (32) pp. 63-78).

The second cassette comprises a gene which, when expressed, can be used as a selectable marker. Numerous selectable markers have been characterised, including some that confer tolerance to antibiotics and others that confer tolerance to herbicides. Examples of suitable selectable marker genes include those that confer tolerance to—hygromycin, kanamycin or gentamycin. Further suitable selectable markers include genes that confer resistance to herbicides such as glyphosate-based herbicides or resistance to toxins such as eutypine. Other forms of selection are also available such as hormone based selection systems such as the Multi Auto Transformation (MAT) system of Hiroyrasu Ebinuma et al. (1997) PNAS Vol. 94 pp. 2117-2121; visual selection systems which use the known green fluorescence protein, β glucoronidase and any other selection system such as mannose isomerase (Positech™), xylose isomerase and 2-deoxyglucose (2-DOG). In one embodiment of the present invention, the selectable marker gene is one that confers tolerance to hygromycin. Further expression cassettes are optionally comprised in the COT102 event. For example these may provide other desirable benefits such as herbicide resistance.

The first and second expression cassettes may be introduced into the plant on the same or different plasmids. If the first and second expression cassettes are present on the same plasmid and introduced into the plant via an *Agrobacterium*-mediated transformation method, they may be present within the same or different T-DNA regions. In one embodiment of the present invention, the first and second expression cassettes are present on the same T-DNA region.

According to the first aspect of the invention, there is provided a polynucleotide comprising at least 17 contiguous nucleotides from the 26-nucleotide sequence of SEQ ID NO: 1. In one embodiment said polynucleotide comprises at least 18 contiguous nucleotides from SEQ ID NO: 1. In a further embodiment said polynucleotide comprises at least 20 contiguous nucleotides from SEQ ID NO: 1. In a still further embodiment said polynucleotide comprises at least 22 contiguous nucleotides from SEQ ID NO: 1. In yet a further embodiment said polynucleotide comprises at least 24 contiguous nucleotides from SEQ ID NO: 1. In a still further embodiment there is provided a polynucleotide comprising the sequence of SEQ ID NO: 1.

In a further aspect of the invention, there is provided a polynucleotide comprising at least 17 contiguous nucleotides from the 26-nucleotide sequence of SEQ ID NO: 2. In one embodiment said polynucleotide comprises at least 18 contiguous nucleotides from SEQ ID NO: 2. In a further embodiment said polynucleotide comprises at least 20 contiguous nucleotides from SEQ ID NO: 2. In a still further embodiment said polynucleotide comprises at least 22 contiguous nucleotides from SEQ ID NO: 2. In yet a further embodiment said polynucleotide comprises at least 24 contiguous nucleotides from SEQ ID NO: 2. In a still further embodiment there is provided a polynucleotide comprising the sequence of SEQ ID NO: 2.

In a further aspect of the present invention there is provided a polynucleotide as described above comprising the sequence of SEQ ID NO: 7. In a still further aspect of the present invention, there is provided a polynucleotide as described above comprising the sequence of SEQ ID NO: 21.

In another aspect of the present invention there is provided a plant comprising a polynucleotide which comprises at least 17 contiguous nucleotides of SEQ ID NO: 1 and/or SEQ ID NO: 2. In one embodiment said plant comprises at least 18 contiguous nucleotides of SEQ ID NO: 1 and/or SEQ ID NO: 2. In a further embodiment said plant comprises at least contiguous nucleotides of SEQ ID NO: 1 and/or SEQ ID NO: 2. In a further embodiment said plant comprises at least 22 contiguous nucleotides of SEQ ID NO: 1 and/or SEQ ID NO: 2. In a still further embodiment said plant comprises at least 24 contiguous nucleotides of SEQ ID NO: 1 and/or SEQ ID NO: 2. In yet a further embodiment said plant comprises the sequence of SEQ ID NO: 1 and/or SEQ ID NO: 2. In a further embodiment still, said plant additionally comprises the sequence of SEQ ID NO: 7. In another embodiment, said plant comprises the sequence of SEQ ID NO: 21. In one embodiment of the present invention, said plant is a cotton plant. In a further embodiment, said plant is an insecticidal cotton plant which is the COT102 event, or a plant derived therefrom.

The skilled man is familiar with plant transformation methods. In particular, two principal techniques have been characterised across a wide range of plant species: transformation by *Agrobacterium* and transformation by direct DNA transfer.

*Agrobacterium*-mediated transformation is a commonly used method for transformation of dicotyledonous plants. The foreign DNA to be introduced into the plant is cloned into a binary vector in between left and right border consensus sequences. This is the T-DNA region. The binary vector is transferred into an *Agrobacterium* cell, which is subsequently used to infect plant tissue. The T-DNA region of the vector comprising the foreign DNA is inserted into the plant genome. The marker gene cassette and trait gene cassette may be present on the same T-DNA region, different T-DNA regions in the same vector, or even different T-DNA regions in different vectors. In one embodiment of the present invention, the cassettes are present on the same T-DNA region.

Alternatively, direct DNA transfer can be used to introduce the DNA directly into a plant cell. One suitable method of direct transfer may be bombardment of plant cells with a vector comprising the DNA for insertion using a particle gun (particle-mediated biolistic transformation); another established method, 'whiskers', involves coating the DNA onto silicon carbide fibres onto which cells are impaled. Other methods for transforming plant cells include protoplast transformation (optionally in the presence of polyethylene glycols); sonication of plant tissues, cells or protoplasts in a medium comprising the polynucleotide or vector; micro-insertion of the polynucleotide or vector into plant material (optionally employing the known silicon carbide "whiskers" technique), electroporation and the like.

Following transformation, transgenic plants must be regenerated from the transformed plant tissue, and progeny possessing the foreign DNA selected using an appropriate marker such as resistance to hygromycin. The skilled man is familiar with the composition of suitable regeneration media.

A plant of this aspect of the invention, as described herein, has an insecticidal effect on insects from one or more species from the group comprising *Heliothis* sp., *Helicoverpa* sp. and *Spodoptera* sp. which may infest it. "Infest" as used herein refers to attack, feeding or damage in any way by one or more insects. Thus, for example, the plant of the present invention will provide a self-defence mechanism against infestation by pest insects such as *Helicoverpa zea* (cotton boll worm). As a result, a reduced number of insecticide sprays are required during the cultivation of said plant compared to a non-transgenic cotton plant of the same variety and yield loss through insect pests is kept at a minimal level.

The present invention is not limited to the COT102 event itself, but is further extended to include any plant material derived therefrom, including seeds in so far as they contain at least one of the present inventive polynucleotides. The present invention includes, but is not limited to plants that are derived from a breeding cross with the COT102 event or a derivative therefrom by conventional breeding or other methods. The invention also includes plant material derived from the COT102 event that may comprise additional, modified or fewer polynucleotide sequences compared to the COT102 event or exhibit other phenotypic characteristics. For example it may be desirable to transform the plant material derived from the COT102 event to generate a new event that possesses an additional trait, such as a second insect resistance gene. This process is known as gene stacking. The second insect resistance gene may encode, for example insecticidal lectins, insecticidal protease inhibitors and insecticidal proteins derived from species of the *Bacillus thuringiensis, Xenorhabdus nematophilus*, or *Photorabdus luminescens*. Preferably, the second insect resistance gene encodes a Cry gene from the bacterium *Bacillus thuringiensis*, which Cry gene produces a toxin with a different mode of action or binding site in the insect gut to VIP for the control of different insect species.

The present invention further provides plant material derived from the COT102 event which possesses an additional trait such as herbicide resistance, nematode resistance or fungal resistance. In one embodiment, said additional trait is herbicide resistance. In a further embodiment, said herbicide resistance trait provides resistance to a herbicide which comprises glyphosate acid or an agriculturally acceptable salt thereof. In a further embodiment still, said herbicide resistance trait is provided by a gene encoding EPSP synthase or a mutant thereof.

The present invention further provides a method of controlling insects comprising providing plant material derived from the COT102 event at a locus where said insects feed. The invention yet further provides a method of controlling insects comprising providing plant material derived from the COT102 event at a locus where said insects feed, and applying other agrochemicals to said plant material such as herbicides, fungicides and other insecticidal compounds including other insecticidal proteins. Examples of possible insecticidal compounds include insecticidal lectins, insecticidal protease inhibitors and insecticidal proteins derived from species of the *Bacillus thuringiensis, Xenorhabdus nematophilus*, or *Photorabdus luminescens*. Examples of possible chemicals include pyrethroids, carbamates, imidacloprid, organochlorines, and macromolecules such as spinosad, abamectin or emamectin.

According to yet a further aspect of the present invention, there is provided a method of detecting plant material derived from the COT102 transgenic event comprising obtaining a sample for analysis; extracting DNA from the sample; providing a pair of primers designed to bind to a polynucleotide comprising at least 17 contiguous nucleotides of SEQ ID NO: 1 and/or SEQ ID NO: 2; amplifying the region which lies between the sites at which the primers bind; and detecting the presence of the amplification product. Suitable pairs of primers for use in this method of detection can be designed using parameters well known to those skilled in the art of molecular biology now that SEQ ID NOs 1 and 2 are made available. For example, one or both primers of the pair may be designed to be vector-specific, trait gene specific, promoter specific, specific to the sequence of the junction between the inserted DNA and the genomic DNA, and/or marker specific. In one embodiment, the sequence of said primers is depicted as SEQ ID NO: 3 and SEQ ID NO: 4.

In an embodiment of the present invention, the region amplified by said method (the 'amplicon') is between 300 and 1000 base pairs in length. In a further embodiment the amplicon is between 500 and 900 base pairs in length. In a still further embodiment the amplicon is 800 base pairs in length. In a further embodiment the amplicon is produced using the above method in conjunction with the primers of the sequence of SEQ ID NO: 3 and SEQ ID NO: 4, and is 800 base pairs in length.

Alternative primers which may be used in combination to detect the COT102 event include SEQ ID NOs 18 and 19 which are specific for the COT102 event and produce a 962 bp amplicon, SEQ ID NOs 22 and 23 which are specific for the VIP gene and produce a 556 bp amplicon, or SEQ ID NOs 24 and 25 which are specific for the gene conferring resistance to the antibiotic hygromycin and produce a 367 bp amplicon.

There are many amplification methods that may be used in accordance with this aspect of the invention. The underlying principle, a known technique to those skilled in the art, is the polymerase chain reaction (PCR). The amplification product from a PCR reaction may be visualised by staining with ethidium bromide and excitation with UV light, typically after size separation using agarose gel electrophoresis.

An embodiment of the present invention employs variations of the PCR principle such as TaqMan™. This involves labelling at least one of the primers involved in the amplification process with a fluorescent dye. When unbound, the primer adopts a conformation such that no fluorescence can be detected. However, when the primer is bound to a piece of DNA, the conformation changes and fluorescence can be detected. In this way, the amplification process can be monitored in real-time, the intensity of fluorescence corresponding directly to the level of amplification. Further embodiments of the present invention include, but are not limited to, RACE PCR.

A further embodiment of the present invention involves the use of multiplex PCR for distinguishing between homozygous COT 102 plant material and heterozygous COT102 plant material. This is known to those skilled in the art as zygosity testing, and involves the use of three PCR primers which bind to specific parts of the cotton genome and/or inserted DNA. Suitable primers for use in such a zygosity test are depicted as SEQ ID NOs 18 to 20.

In another aspect of the invention there is provided a method of detecting plant material derived from the COT102 event comprising obtaining a sample for analysis; providing a probe designed to bind to the complement of a polynucleotide which comprises at least 17 contiguous nucleotides of SEQ ID NO: 1 and/or SEQ ID NO: 2 when said polynucleotide is single stranded; hybridising said probe with the sample; and detecting whether the probe has hybridised. In one embodiment, said probe comprises the sequence of SEQ ID NO: 1 and/or SEQ ID NO: 2. In an embodiment of the present invention there is provided a method of detecting plant material derived from the COT102 event using a probe selected from the group comprising SEQ ID NO: 5, SEQ ID NO: 6 and SEQ ID NO: 7. In one embodiment, said probe comprises SEQ ID NO: 5. In a further embodiment, said probe consists of SEQ ID NO: 5. The probe may be, for example, a PCR product or restriction digestion fragment. In a further embodiment, the probe as described herein may be tagged with a fluorescent, radioactive, enzymatic or other suitable label to enable hybridisation to be detected. The skilled man will know how to design suitable probes, now that he has the benefit of the present disclosure.

In a further embodiment of the present invention, there is provided a method of hybridising a probe to the sample under stringent conditions and detecting whether the probe has hybridised. Stringent hybridisation conditions are well known to the skilled man and comprise, for example: hybridisation at a temperature of about 65° C. in a solution containing 6×SSC, 0.01% SDS and 0.25% skimmed milk powder, followed by rinsing at the same temperature in a solution containing 0.2×SSC and 0.1% SDS.

Suitable techniques for detecting plant material derived from the COT102 event based on the hybridisation principle include, but are not limited to Southern Blots, Northern Blots and in-situ hybridisation. The skilled man is familiar with techniques such as these. Typically, they involve incubating a probe with a sample, washing to remove unbound probe, and detecting whether the probe has hybridised. Said detection method is dependent on the type of tag attached to the probe—for example, a radioactively labelled probe can be detected by exposure to and development of x-ray film. Alternatively, an enzymatically labelled probe may be detected by conversion of a substrate to effect a colour change.

In a further aspect of the invention there is provided a method of detecting plant material derived from the COT102 event comprising obtaining a sample for analysis; providing an antibody designed to bind to a VIP protein contained within a plant comprising at least 17 contiguous nucleotides from SEQ ID NO: 1 and/or SEQ ID NO: 2; incubating said antibody with the sample; and detecting whether the antibody has bound. In one embodiment of the present invention said VIP protein comprises the sequence of SEQ ID NO: 8.

Suitable methods of detecting plant material derived from the COT102 event based on said antibody binding include, but are not limited to Western Blots, Enzyme-Linked ImmunoSorbent Assays (ELISA) and SELDI mass spectrometry. The skilled man is familiar with these immunological techniques. Typical steps include incubating a sample with an antibody that binds to the VIP protein, washing to remove unbound antibody, and detecting whether the antibody has bound. Many such detection methods are based on enzymatic reactions—for example the antibody may be tagged with an enzyme such as horse radish peroxidase, and on application of a suitable substrate, a colour change detected. Suitable antibodies may be monoclonal or polyclonal.

In another aspect of the invention there is provided a method of detecting plant material derived from the COT102 event comprising obtaining a sample for analysis; making a protein extract of the sample; providing a test strip designed to detect the presence of a VIP protein present within the sample; incubating the test strip with the sample; and detecting whether VIP protein is present. In one embodiment of the present invention said VIP protein comprises the sequence of SEQ ID NO: 8.

An alternative antibody-based detection method for COT102 uses of dipsticks or test strips. Typical steps include incubating a test strip with a sample and observing the presence or absence of coloured bands on the test strip. The coloured bands are indicative of the presence of a protein in the sample. Such dipstick or test strip tests are protein specific, and may be used for rapid testing of samples in the field.

In a further aspect of the present invention there is provided a method of detecting plant material derived from the COT102 event comprising obtaining a sample for analysis; subjecting one or more insects of the species *Spodoptera frugiperda* (susceptible to VIP3A) to the sample; subjecting one or more insects of species *Ostrinia nubilalis* (not susceptible to VIP3A) to the sample as a control; detecting whether the sample has an insecticidal effect on insects from each species; and comparing the results with an authentic COT102 bioassay profile. The results are compared against an authentic COT102 bioassay profile that is produced using insects of the same condition which have been subjected to the same dose and type of COT102 plant material and where the insecticidal effect is detected the same length of time after subjecting the insects to the COT102 sample. *Spodoptera frugiperda* is a positive control for COT102 as it is susceptible to a suitable dose of VIP3A, while *Ostrinia nubilalis* is a negative control for COT102 as it is not susceptible to a suitable dose of VIP3A.

In one embodiment of the invention, the method of detecting plant material derived from the COT102 event includes but is not limited to leaf-feeding bioassays in which a leaf or other suitable plant part from the COT102 event or any plant material derived from the COT102 event, is infested with one or more pest insects. Detection may be through assessment of damage to the leaf or plant part after set time periods, assessment of mortality or another insecticidal effect on the insects. Alternative plant parts which may be used for such bioassays include bolls and squares. Such bioassays may be carried out in the field, or glasshouse, and may be subject to natural or artificial insect infestation.

In another aspect of the invention, there is provided a kit of parts comprising a means for detecting the presence in a sample of plant material derived from the COT102 event. Preferably, said kit of parts comprises a means for detecting the presence in a sample of a polynucleotide comprising at least 17 contiguous nucleotides from the sequence of SEQ ID NO: 1 and/or SEQ ID NO: 2, or a protein encoded by a polynucleotide as described above, or a VIP protein. In an embodiment of the present invention, said kit of parts may comprise DNA amplification-detection technology such as PCR or TaqMan™. In a further embodiment of the present invention, said kit of parts may comprise probe hybridisation-detection technology such as Southern Blots, Northern Blots or in-situ Hybridisation. In another embodiment of the present invention, said kit of parts may comprise antibody binding-detection technology such as Western Blots, ELISA's, SELDI mass spectrometry or test strips. In a further embodiment of the present invention, said kit of parts may comprise insect bioassay-detection technology such as leaf feeding bioassays or mortality bioassays. In a further embodiment of the present invention, said kit of parts may comprise any combination of the afore-mentioned detection technologies. In a still further embodiment, said kit of parts may comprise in the form of instructions one or more of the methods described above.

EXAMPLES

The invention will be further apparent from the following non-limiting examples in conjunction with the associated sequence listings as described below:

SEQ ID NO 1: Polynucleotide sequence which extends across the junction where the 5' end of the COT102 insert is inserted into the cotton genome in event COT102.

SEQ ID NO 2: Polynucleotide sequence which extends across the junction where the 3' end of the COT102 insert is inserted into the cotton genome in event COT102.

SEQ ID NOs 3-4: Polynucleotide sequences suitable for use as primers in the detection of the COT102 event.

SEQ ID NOs 5-7: Polynucleotide sequences suitable for use as probes in the detection of the COT102 event.

SEQ ID NO 8: Amino acid sequence of the VIP3A toxin protein.

SEQ ID NOs 9-17: Polynucleotide sequences suitable for use as TaqMan primers in the detection of the COT102 event.

SEQ ID NOs 18-20: Polynucleotide sequences suitable for use as primers in the detection of the COT102 event via zygosity testing.

SEQ ID NO 21: Polynucleotide sequence characterising COT102 event.

SEQ ID Nos 22-25: Polynucleotide sequences suitable for use as primers in the detection of the COT102 event.

Example 1

Cloning and Transformation 1.1 Vector Cloning

Standard gene cloning techniques of restriction digestion and ligation of fragments from in-house vectors were used to construct the transformation vector, pNOV3001. The vector included a selectable marker cassette comprising a Ubiquitin (UBQ3) promoter, the UBQ3 intron, a gene sequence which encodes a protein conferring resistance to hygromycin, and a nos polyadenylation sequence. The vector also included the expression cassette of the target gene, which cassette comprised an Actin (Act2) promoter, the Act2 intron, a sequence encoding the VIP3A gene that had been codon optimised for expression in maize, and a nos polyadenylation sequence. The selectable marker cassette and VIP3A containing cassette were cloned within the T-DNA region of vector pNOV3001, between the left and right border sequences. The vector also comprised a gene conferring resistance to an antibiotic, spectinomycin, for prokaryotic selection.

The vector was transformed into *Agrobacterium tumefaciens* strain EHA101 using standard *Agrobacterium* transformation techniques, and transformed cells selected through their resistance to spectinomycin.

1.2 Plant Transformation

The COT102 event was produced by *Agrobacterium*-mediated transformation of *Gossypium hirsutum* L. cv Coker 312.

Coker 312 seeds were surface sterilized for 30 seconds in 70% ethanol using enough ethanol to cover the amount of seed to be sterilized. The seeds were washed with ethanol, rinsed in sterile water and soaked in a 12% Clorox+Tween 20 solution for 20 minutes. This washing procedure was performed 3 times. Seeds were then placed onto germination medium (Stewart and Hsu, 1977) and allowed to germinate at 30° C. for 7-10 days.

2 ml cultures of *Agrobacterium* containing the pNOV3001 construct were grown overnight in appropriate antibiotics and then diluted with MSNH medium (19:1) in a sterile petri dish. Hypocotyls were cut into 6-8 mm lengths and placed in the diluted *Agrobacterium* solution for at least 30 seconds. Hypocotyl explants were removed from the *Agrobacterium* solution and blotted on sterile filter paper to remove excess bacteria. Hypocotyls were placed onto T2 medium (MS salts, B5 vitamins, 0.1 mg/L 2, 4-D, 0.5 mg/L kinetin, 30 g/L glucose, 2 g/L Phytagel—pH 5.8) and co-cultured with the *Agrobacterium* for 72 hours in the dark.

Hypocotyl explants were again blotted on sterile filter paper and transferred to plates containing MS2NK medium (MS salts, B5 vitamins, 2 mg/L NAA, 0.1 mg/L kinetin, 30 g/L glucose, 2 g/L Phytogel, 500 mg/L cefotaxime, 10 mg/L hygromycin—pH 5.8). The plates were wrapped with parafilm and incubated in the light at 30° C. for several months until callus was formed.

Callus was broken up as small as possible and placed in a 50 ml Erlenmeyer flask containing 10 ml of liquid MSNH medium (MS salts, B5 vitamins; 30 g/L glucose—pH 5.8). The suspended callus was shaken at 110 rpm in the light at 30° C. until small white slightly round cell clusters were visible. Cells were washed and plated onto solid MSNH medium (MS salts, B5 vitamins, 30 g/L glucose, 2 g/L Phytogel—pH 5.8). Plates were checked monthly for somatic embryo development.

Mature somatic embryos were picked from the plates and placed onto plates containing SA medium (Stewart and Hsu salts, 20 g/L sucrose, 20 g/L agar—pH 5.8). The plates of embryos were placed in the dark for approximately 14 days. Roots were trimmed from the maturing embryos and the embryos were transferred to SGA medium (Stewart and Hsu salts, 5 g/L sucrose, 1.5 g/L Phytogel, 5 g/L agar—pH 6.8).

After the first true leaf emerged, young plants were moved to pint sized canning jars containing SGA medium. When the plants reached 7-10 cm in height, the top was cut off and transferred to another jar. On developing a good root system, the thus rooted cuttings were transplanted into pots and grown in the greenhouse.

1.3 Identification and Selection of Transgenics

Putative transgenic plants were screened by PCR for the presence of the VIP3A gene. Positive events were identified and screened using insect bioassays for insecticidal activity against Fall Armyworm (*Spodoptera frugiperda*) (see Example 7). Insecticidal lines were characterized for copy number by TaqMan™ analysis (see Example 2). T1 seed from 3 single copy & 2 double copy events were observed in a field trial for insect resistance and agronomic quality. Two events, COT101 and COT102, were chosen based on having a single copy of the transgene, good protein expression as identified by ELISA (see Example 4), good insecticidal activity against Cotton Boll Worm (*Helicoverpa zea*) and field performance. At the end of the second year of field trials, results between the two events were compared and COT102 was progressed.

1.4 Verification of Sequence of COT102

Genomic DNA was isolated from the COT102 event. This was used in the sequencing of the junctions of the DNA insertion site with the cotton genomic DNA in the COT102 event, using standard DNA sequencing techniques.

Example 2

COT102 Detection Via TaqMan™

2.1 DNA Extraction

DNA was extracted from leaf tissue using the Wizard™ Magnetic 96 DNA Plant System (Promega, #FF3760), according to the manufacturers instructions, with an additional step at the beginning of the protocol: following grinding of the leaf material, 0.9 ml Cotton Extraction Buffer (0.2M Tris pH 8.0, 50 mM EDTA, 0.25M NaCl, 0.1% v/v 2-mercaptoethanol, 2.5% w/v polyvinyl-pyrrolidone) was added to each well, the plant tissue resuspended and the plate centrifuged at 4,000 rpm (2755 g) for 10 minutes. After aspirating and discarding the supernatant, 300 ul Lysis Buffer A (Promega) was added and the manufacturers protocol was followed from this point. This procedure resulted in approximately 85 ul of purified genomic DNA at a concentration of approximately 10 ng/ul.

2.2 TaqMan PCR Reactions

TaqMan™ PCR reactions were setup using a standard reaction mix comprising:

625 ul 2× Jumpstart Master Mix for Q-PCR (Sigma, #P2893), supplemented with 15 mM $MgCl_2$ and 200 nM Strata-ROX 25 ul 50×FAM primer/probe mix 25 ul 50×TET primer/probe mix 200 ul Water.

50× primer/probe mixes comprise 45 ul of each primer at a concentration of 1 mM, 50 ul of the probe at a concentration of 100 uM and 860 ul 1×TE, and were stored in an amber tube at 4° C. Examples of suitable primer/probe sequence combinations which were used are:

| Primer Name | Primer Sequence 5'-3' | SEQ ID |
|---|---|---|
| GhCH12b-F Forward | GGTCCCTGGATACGGTGTCA | SEQ ID NO: 9 |
| GhCH12b-R Reverse | TTGAGGGTTGGATCCTTTGC | SEQ ID NO: 10 |
| GhCH12b-TET Probe | CCAACATCATCAATGGTGGCA TCGAAT (5' label = TET, 3' label = TAMRA) | SEQ ID NO: 11 |
| Hygromycin-F Forward | CAGGCAGGTCTTGCAACGT | SEQ ID NO: 12 |
| Hygromycin-R Reverse | CGAGAGCCTGACCTATTGCAT | SEQ ID NO: 13 |
| Hygromycin-FAM Probe | ACACCCTGTGCACGGCGGG (5' label = FAM, 3' label = TAMRA) | SEQ ID NO: 14 |
| Vip3-F Forward | ATGAAGACCCTGCGCTACGA | SEQ ID NO: 15 |
| Vip3-R Reverse | ACGCCCAGTGGCATGTAGA | SEQ ID NO: 16 |
| Vip3-FAM Probe | AGCGAGGCCGAGTACCGCACC (5' label = FAM, 3' label = TAMRA) | SEQ ID NO: 17 |

7 ul of master mix was dispensed into each well of a 384-well TaqMan™ assay plate. 3 ul DNA template was added to the appropriate wells. 3 ul of copy control dilution series was added to specific wells as a control. The reactions were run in an ABI7900 (Applied Biosystems) using the following cycling conditions:

| Step | Temperature | Time |
|---|---|---|
| 1 | 50° C. | 2 min |
| 2 | 95° C. | 10 min |
| 3 | 95° C. | 15 sec |
| 4 | 60° C. | 1 min |
| 5 | Goto step 3, repeat 40 times | |

Data was analysed using SDS2.0 software (Applied Biosystems).

Example 3

COT102 Detection Via PCR 3.1 Genomic DNA Extraction

Genomic DNA from COT102 was extracted as described in Example 2.1.

3.2 Multiplex PCR Zygosity Test

PCR primers were designed to bind to cotton genomic DNA sequence upstream of the site at which the COT102 cassette inserted (SEQ ID NO: 18); the COT102 cassette sequence itself (SEQ ID NO: 19); and cotton genomic DNA sequence which is replaced when the COT102 sequence is inserted (SEQ ID NO: 20). When the COT102 insert is present, primer pairs SEQ ID NO: 18 and 19 amplify a PCR fragment of 962 bp in size. A 50 ul PCR reaction was set up for each sample to be tested as follows:

| | |
|---|---|
| 1x JumpState ReadyMix REDTaq PCR (Sigma P-1107) | 25 ul |
| 40 pmole primer 1 (SEQ ID NO: 18) | 4 ul |
| 40 pmole primer 2 (SEQ ID NO: 19) | 4 ul |
| 40 pmole primer 3 (SEQ ID NO: 20) | 4 ul |
| 40 ng genomic DNA | 4 ul |
| ddH2O | 9 ul |

The PCR reactions were heated in a thermocycler at 94° C. for 2 minutes, followed by 35 cycles as follows: 94° C. for 30 seconds, 60° C. for 30 seconds, 72° C. for 1 minute. The reaction was completed by heating at 72° C. for 5 minutes.

3.3 Analysis

PCR reactions were run on an agarose gel, and DNA bands visualised under UV light after staining with ethidium bromide. The presence of 3 bands indicated that the sample was a COT102 homozygote plant; 2 bands (one of which being 962 bp in size) indicated that the sample was a COT102 heterozygote plant; 2 bands (with no band of 962 bp in size) indicated that the sample was a homozygote wild type cotton plant.

3.4 Event Specific PCR

One PCR primer was designed to bind towards the 3' end of the VIP3A gene (SEQ ID NO: 3). Another PCR primer was designed to bind to the complementary strand of the flanking genomic DNA sequence downstream of the 3' end of the COT102 insertion site (SEQ ID NO: 4). These primers were used together in a PCR reaction using COT102 genomic DNA resulting in the amplification of an 800 bp fragment. When the primers were used in a PCR reaction using a Coker312 non-transformed cotton genomic DNA sample, no fragment was amplified.

In a second pair of primers, one primer was designed to bind to the hygromycin gene (SEQ ID NO: 19) and the other primer was designed to bind to the flanking genomic DNA sequence upstream of the 5' end of the COT102 insertion site (SEQ ID NO: 18). These primers were used together in a PCR reaction using COT102 genomic DNA resulting in the amplification of a 962 bp fragment. When the primers were used in a PCR reaction using a Coker312 non-transformed cotton genomic DNA sample, no fragment was amplified.

Example 4

COT102 Detection Via Southern Blot 4.1 DNA Extraction for Use in Southern Blotting Approximately 5 to 10 grams of plant tissue was ground in liquid nitrogen using a mortar and pestle. The plant tissue was resuspended in 12.5 ml extraction buffer A (0.2M Tris pH8.0, 50 mM EDTA, 0.25M NaCl, 0.1% v/v B-mercaptoethanol, 2.5% w/v Polyvinyl-pyrrolidone), and centrifuged for 10 minutes at 4,000 rpm (2755 g). After discarding the supernatant the pellet was resuspended in 2.5 ml Extraction Buffer B (0.2M Tris pH8.0, 50 mM EDTA, 0.5M NaCl, 1% v/v B-mercaptoethanol, 2.5% w/v Polyvinyl-pyrrolidone, 3% Sarkosyl, 20% Ethanol) and incubated at 37° C. for 30 minutes. During incubation, the sample was mixed once with a sterile loop. After incubation an equal volume of chloroform/isoamyl alcohol (24:1) was added, mixed gently by inversion, and centrifuged for 20 minutes at 4,000 rpm. The aqueous layer was collected, and 0.54 volume isopropanol added followed by centrifugation for 5 minutes at 4,000 rpm to precipitate the DNA. The supernatant was discarded and the DNA pellet resuspended in 500 ul TE. In order to degrade any RNA present, the DNA was incubated at 37° C. for 30 minutes with 1 ul 30 mg/ml RNase A, centrifuged for 5 minutes at 4,000 rpm and precipitated by centrifugation at 14,000 rpm for 10 minutes in the presence of 0.5 volume 7.5M ammonium acetate and 0.54 volume isopropanol. After discarding the supernatant, the pellet was washed with 500 ul 70% ethanol and allowed to dry before resuspending in 100 ul TE.

4.2 Restriction Enzyme Digests

The DNA was quantified using a spectrophotometer or fluorometer (using 1×TNE and Hoechst dye). Suitable enzyme digests were prepared using Bug DNA per digest in a total volume of 50 ul. Digests included BamHI, EcoRI, EcoRV, HindIII, NcoI, SacI, ScaI, SpeI and PstI, both alone and in combination. In particular, a BamHI and EcoRI double digest was used to detect the intactness of the VIP3A gene; a BamHI and EcoRV double digest was used to detect VIP3A locus number and intactness of the hygromycin gene; and a BamHI single digest was used to detect VIP3A locus number. Digests were incubated overnight at the appropriate temperature for each enzyme. Samples were spun in a speed vacuum to reduce the volume to 30 ul.

4.3 Gel Electrophoresis

Bromophenol blue loading dye was added to each sample from 4.2 above, and each sample loaded on a 0.8% TBE agarose gel containing ethidium bromide. The gel was run at 60 volts overnight.

The gel was washed in 0.25M HCl for 15 minutes to depurinate the DNA, and then washed with water. A Southern Blot was set up as follows: 20 sheets of thick dry blotting paper was placed in a tray and 4 sheets of thin dry blotting paper placed on top. One sheet of thin blotting paper was pre-wet in 0.4M NaOH and placed on top of the stack, followed by a sheet of Hybond-N+ transfer membrane (Amersham Pharmacia Biotech, #RPN303B), also pre-wet in 0.4M NaOH. The gel was placed on top ensuring that there were no air bubbles between the gel and the membrane. Three further sheets of pre-soaked blotting paper were placed on top of the gel and the buffer tray filled with 0.4M NaOH. Connecting the gel stack with the buffer tray using a wick pre-soaked in 0.4M NaOH started the transfer of DNA to the membrane. DNA transfer took place for approximately 4 hours at room temperature. Following transfer, the Hybond membrane was rinsed in 2×SSC for 10 seconds and the DNA bound to the membrane via UV cross-linking.

4.4 Hybridisation

A suitable DNA probe was prepared by PCR. 25 ng probe DNA in 45 ul TE was boiled for 5 minutes, placed on ice for 7 minutes then transferred to a Rediprime II (Amersham Pharmacia Biotech, #RPN1633) tube. After addition of 5 ul P32-labelled dCTP to the Rediprime tube, the probe was incubated at 37° C. for 15 minutes. The probe was purified by centrifugation through a microspin G-50 column (Amersham Pharmacia Biotech, #27-5330-01) according to the manufacturers instructions to remove unincorporated dNTPs. The activity of the probe was measured using a scintillation counter.

The Hybond membrane was pre-hybridised by wetting with 20 ml pre-warmed Church pre-hybridisation solution (500 mM $NaPO_4$, 1 mM EDTA, 7% SDS, 1% BSA) at 65° C. for 30 minutes. The labelled probe was boiled for 5 minutes, and placed on ice for 10 minutes. An appropriate amount of probe (1 million counts per 1 ml pre-hybridisation buffer) was added to the pre-hybridisation buffer and hybridisation occurred at 65° C. overnight. The following day, the hybridisation buffer was discarded, and following a rinse with 20 ml Church Wash Solution 1 (40 mM $NaPO_4$, 1 mM EDTA, 5% SDS, 0.5% BSA), the membrane washed in 150 ml Church Wash Solution 1 at 65° C. for 20 minutes. This process was repeated twice with Church Wash Solution 2 (40 mM. NaPO4, 1 mM EDTA, 1% SDS). The membrane was exposed to a phosphor screen or X-ray film to detect where the probe has bound.

Example 5

COT102 Detection Via ELISA 5.1 Protein Extraction

Cotton tissue for analysis was harvested and frozen at −70° C. Fresh tissue was ground to a fine powder and weighed into a labelled polypropylene tube. Extraction buffer (100 mM Tris, 100 mM Sodium Borate, 5 mM MgCl, 0.05% Tween 20, 0.2% Sodium Ascorbate, Water, pH 7.8, 1 mM AEBSF, 0.001 mM Leupeptin) was added to the sample in a ratio of 2:1 (volume extraction buffer:sample fresh weight) for fresh tissue or 30:1 (volume extraction buffer:sample dry weight) for lyophilised tissue. The sample was vortexed and homogenised using a Brinkman PT 10/35 Polytron equipped with a PTA 10TS foam-reducing generator, until the mixture became liquefied. Extracts were centrifuged at 10,000×g for 15 minutes. The protein extract supernatant was stored at 2-8° C.

5.2 ELISA Protocol

The ELISA procedure used standard techniques as follows. A 96-well plate was soaked in ethanol for 2 hours, and air-dried. The plate was coated with 50 ul goat anti-VIP3A antibody per well and incubated overnight at 2-8° C. After washing three times with 1×ELISA wash solution (100 mM Tris, 0.5% Tween-20, 75 mM NaCl, pH8.5), the plate was dried briefly by tapping upside down on a paper towel. 150 ul blocking solution (10 mM $NaPO_4$, 140 mM NaCl, 1% BSA, 0.02% Sodium Azide, titrated to pH7.4 with monobasic NaPi and dibasic NaPi) was added to each well followed by incubation at room temperature for 45 minutes. The plate was washed 3 times as described above.

VIP3A standards and protein extract samples were applied to appropriate wells of the plate in triplicate, 50 ul total volume per well. The plate was incubated at 2-8° C. for 1 hour 30 minutes, followed by room temperature for a further 30 minutes. The plate was washed three times with ELISA wash solution, and then incubated at 35-39° C. for 1 hour with 50 ul rabbit anti-VIP3A antibody per well. The plate was washed three times with ELISA wash solution, and incubated at room temperature for 30 minutes with 50 ul donkey anti-rabbit alkaline phosphatase per well. Following a further three washes with ELISA wash solution, 50 ul phosphatase substrate solution was added per well and the plate incubated for 30 minutes at room temperature. The reaction was stopped by addition of 50 ul 3M NaOH per well. The absorbance of the solution in each well was measured at 405 nm using a Ceres 900C multiwell plate reader and the results analysed using KC3 Curve fitting software (Bio-Tek Instruments Inc.). The concentration of VIP3A in the samples was calculated by reference to the VIP3A protein standards.

Example 6

COT102 Detection Via DipStick 6.1 Protein Extraction

A piece of leaf tissue approximately 2 $cm^2$ was placed in a tube containing extraction buffer. A plastic stirrer was used to extract protein from the tissue, by cutting into and mascerating the tissue.

6.2 Dipstick Test

A test strip was placed into the tube and incubated for 5-10 minutes for the result to develop. The test strip comprised a first band at which anti-VIP3A antibody was bound, and a second band at which a control antibody was bound. After incubation, a double red line in the result window of the test strip indicated that VIP3A was present. The lower line indicated the presence of Vip3A protein while the upper line was a control indicating that the assay was working correctly.

Example 7

COT102 Detection Via Insect Bioassay 7.1 Leaf Bioassays

Leaf assays were performed on Fall Army Worm (*Spodoptera frugiperda*), Cotton Boll Worm (*Helicoverpa zea*) and Tobacco Budworm (*Heliothis virescens*) as follows:

Pads were soaked with 300 ul to 500 ul distilled water and placed into Gelman dishes. Leaf pieces measuring between approximately 0.5 square inches and 0.75 square inches were excised from cotton plants 8 to 12 inches in height, and placed on the pads. Between 8 and 10 insect larvae were placed in each dish and a lid fitted. The dishes were incubated at 28° C. On the third and sixth days after infestation, damage to the leaf in each dish was scored and compared with the control plants.

7.2 Boll Bioassays

Four absorbent pads were saturated with water and placed inside a large plastic cup. Three extra thick glass filters, each soaked with 100 ul distilled water, were placed in a smaller plastic cup, which was then seated inside the larger cup. A 1.25 inch long boll was excised, immersed in 10 mg/ml to 20 mg/ml Nystatin and placed on the filters in the small cup. 50 insect larvae were placed on the square or boll and a lid attached to the larger cup. The squares or bolls were re-infested with 50 more larvae after 7 days.

The experiment was incubated at room temperature for approximately 3 weeks. The bolls were then cut open to determine damage. Damage to the boll was compared to the control samples.

7.3 Lyophilised Leaf Bioassays

Bioassays using freeze-dried leaf tissue were performed on *Heliothis virescens* as follows:

Terminal leaves were snap-frozen on dry-ice at time of picking and lyophilised overnight. The freeze dried tissue was ground in a mortar and pestle to a fine powder and resuspended in 0.2% agar solution to make an 8% (0.08 g/ml) suspension of leaf powder. The suspension was overlaid on top of artificial insect diet in 96-well plates and left to dry. A single neonate insect larva was introduced into each well and the plates sealed. The plates were incubated at 28° C. On the sixth day after infestation, larval mortality was scored and compared with control samples. Results obtained were as follows:

| variety | % leaf powder suspension | % larval mortality (mean of 5 tests) |
|---|---|---|
| Coker 312 | 8 | 6.7 |
| COT102 | 8 | 98.3 |

The invention claimed is:

1. A primer pair for detecting the presence of COT102 nucleic acids in a biological sample, the primer pair comprising a first primer and a second primer designed to bind to a polynucleotide comprising at least 20 contiguous nucleotides of SEQ ID NO: 1 or SEQ ID NO: 2 when said polynucleotide is single stranded, wherein the first primer and the second primer, when used together in a PCR reaction, produce an amplicon that is indicative of COT102 nucleic acids.

2. The primer pair according to claim 1, wherein the first primer is designed to bind to a COT102 insertion sequence and the second primer is designed to bind to a flanking genomic DNA sequence downstream of the 3' end of the COT102 insertion site or to a flanking genomic DNA sequence upstream of the 5' end of the COT102 insertion site.

3. The primer pair according to claim 2, wherein the first primer has the sequence of SEQ ID NO: 3 and the second primer has the sequence of SEQ ID NO: 4.

4. The primer pair according to claim 2, wherein the first primer has the sequence of SEQ ID NO: 19 and the second primer has the sequence of SEQ ID NO: 18.

* * * * *